(12) United States Patent
Argentine et al.

(10) Patent No.: US 7,241,276 B2
(45) Date of Patent: Jul. 10, 2007

(54) PASSIVE HEMOSTATIC SHEATH VALVE (75) Inventors: Jeffery C. Argentine, Petaluma, CA (US); G. Ray Martin, Windsor, CA (US)

(73) Assignee: Trivascular, Inc., Santa Rosa, CA (US)

( * ) Notice: Subject to any disclaimer, the term of this patent is extended or adjusted under 35 U.S.C. 154(b) by 216 days.

(21) Appl. No.: 10/636,871

(22) Filed: Aug. 6, 2003

(65) Prior Publication Data
US 2005/0033239 A1 Feb. 10, 2005

(51) Int. Cl.
A61M 5/178 (2006.01)
(52) U.S. Cl. .................................. 604/167.06
(58) Field of Classification Search ........... 604/500, 604/506–510, 164.01–167.06, 264, 246, 604/247, 256, 523, 533, 537, 284; 606/167
See application file for complete search history.

(56) References Cited

U.S. PATENT DOCUMENTS

| 4,978,341 | A |   | 12/1990 | Niederhauser |
|---|---|---|---|---|
| 5,197,955 | A | * | 3/1993 | Stephens et al. ....... 604/167.01 |
| 5,334,164 | A | * | 8/1994 | Guy et al. .................. 604/248 |
| 5,350,364 | A |   | 9/1994 | Stephens et al. |
| 5,352,215 | A | * | 10/1994 | Thome et al. .............. 604/284 |
| 5,391,154 | A |   | 2/1995 | Young |
| 5,456,284 | A |   | 10/1995 | Ryan et al. |
| 5,603,702 | A |   | 2/1997 | Smith et al. |
| 5,722,958 | A |   | 3/1998 | Gravener et al. |
| 5,865,807 | A | * | 2/1999 | Blake, III ............... 604/167.06 |
| 5,916,198 | A | * | 6/1999 | Dillow .................. 604/167.04 |
| 5,935,112 | A | * | 8/1999 | Stevens et al. ............. 604/256 |
| 5,989,233 | A |   | 11/1999 | Yoon |
| 6,276,661 | B1 |   | 8/2001 | Laird |
| 6,520,939 | B2 |   | 2/2003 | Lafontaine |
| 6,592,544 | B1 |   | 7/2003 | Mooney et al. |
| 6,602,240 | B2 |   | 8/2003 | Hermann et al. |
| 2003/0014015 | A1 |   | 1/2003 | Tansey, Jr. et al. |
| 2003/0171721 | A1 |   | 9/2003 | Enomoto et al. |

FOREIGN PATENT DOCUMENTS

| WO | WO 03/008035 A1 | 1/2003 |
|---|---|---|
| WO | WO 03/039645 A1 | 5/2003 |

* cited by examiner

Primary Examiner—Loan H. Thanh
(74) Attorney, Agent, or Firm—RatnerPrestia (57) ABSTRACT Vascular introducer sheaths incorporating improved passive valves which can maintain hemostasis around medical instruments. A passive sheath valve for creating a hemostatic seal around a medical instrument including a valve body having an upstream end, a downstream end, and a lumen having an inner and outer surface therethrough. The valve body defines a sealing aperture that is configured nominally to remain open. The upstream end includes an upstream annulus region defining at least one opening and the downstream end includes a downstream annulus region. Each annulus region and lumen outer surface define at least one chamber. The at least one opening transmits pressure from the upstream end through the upstream annulus region so as to allow a fluid to enter the at least one chamber.

18 Claims, 6 Drawing Sheets

PASSIVE HEMOSTATIC SHEATH VALVE

BACKGROUND OF THE INVENTION

1. Field of the Invention

The present invention is generally related to medical devices and methods. More particularly, the present invention relates to vascular introducer sheaths incorporating improved passive valves that can maintain hemostasis around medical instruments.

Vascular introducer sheaths are well known components of vascular access systems that are used in a wide variety of diagnostic and therapeutic vascular procedures. For example, introducer sheaths are used in a number of minimally invasive procedures such as endovascular procedures and laparoscopic surgery. Of specific interest relative to the present invention is the endovascular placement of grafts, stents, stent-grafts, and other endoluminal prostheses. Such procedures are often performed through vascular access systems that include an introducer sheath to provide access to a body lumen (e.g., blood vessels), cavity, or organ. A sealing valve typically is located at a proximal portion of the introducer sheath. When medical instruments or tools are inserted into or withdrawn from the sealing valve, the valve generally prevents fluid from inadvertently leaving (e.g., back bleeding) or entering the body lumen through the introducer sheath.

Current introducer sheath valves generally fall into two basic categories: passive and active. A passive valve generally relies on the deformation of a resilient sealing body by the medical instrument inserted through the valve to form the desired fluid tight seal. Active medical valves include a mechanism that moves a sealing body into contact with the traversing medical instrument.

A wide variety of passive and active sealing valve structures for use with introducer sheaths have been proposed. These structures provide different hemostatic valve designs that typically vary in terms of the valve shape, aperture or slit geometry, aperture or slit position, and other design aspects. While these structures have met with varying degrees of success and acceptance, they generally still suffer from disadvantages of leakage around the sealing valve.

For these and other reasons, it is desirable to provide improved introducer sheath hemostatic valves for use in endovascular, laparoscopic, and other medical procedures. It would be particularly desirable if these improved valves provide enhanced hemostasis sealing (i.e., preventing leakage of fluid from or into the introducer sheath), maximize safety, and do not require any actuation in the various modes of operation. It would be further desirable if these improved valve structures were better adapted for passing instruments both distally and proximally therethrough as well as for providing a fluid-tight seal across a wide range of medical instrument diameters.

2. Description of the Background Art

Valve sealing structures for sheaths, catheters, cannulas, trocar assemblies, sheaths, and other medical devices are described in U.S. Pat. Nos. 4,978,341; 5,350,364; 5,391,154; 5,456,284; 5,603,702; 5,722,958; 5,865,807; 5,916,198; 5,935,112; 5,989,233; 6,276,661 B1; and 6,520,939 B2, in U.S. Publication No. US 2003/0014015 A1, and in PCT Publication No. WO 03/008035 A1.

The full disclosures of each of the above references are incorporated herein by reference.

BRIEF SUMMARY OF THE INVENTION

The present invention provides vascular introducer sheaths incorporating improved passive valves which can maintain hemostasis around medical instruments. In particular, the hemostatic valves of the present invention provide secure and reliable sealing so at to minimize leakage of fluid from (e.g., back bleeding) or into the introducer sheath when various instruments or tools are inserted into or withdrawn through the sealing valve. Further, these hemostatic valves provide easy loading of instruments both distally and proximally therethrough, a fluid-tight seal across a wide range of medical instrument diameters, and do not require any actuation mechanisms for sealing.

In one aspect of the present invention, a passive valve for creating a hemostatic seal around a medical instrument is provided. The valve is configured to be removably housed within an introducer sheath. The valve comprises a valve body having an upstream end, a downstream end, and a lumen having an inner and outer surface therethrough. The valve body defines a sealing aperture or hole that is configured nominally to remain open. The upstream end includes an upstream annulus region defining at least one opening and the downstream end includes a downstream annulus region. Each annulus region and lumen outer surface define at least one chamber. The at least one opening transmits pressure from the upstream end through the upstream annulus region so as to allow a fluid (e.g., blood) to enter the at least one chamber as a greater pressure is generally on the upstream side.

The opening advantageously allows for pressure equalization on the upstream and downstream ends of the valve body so that the valve body is less likely to inflate and leak fluids from or into the introducer sheath when medical tools are inserted into or withdrawn from the sealing valve. Moreover, filling of the chamber via the opening enhances the fluid tight hemostatic seal around the medical instrument. The sealing aperture facilitates easy loading of instruments both distally and proximally. In one embodiment of the present invention, the upstream annulus region defines four pressure equalization openings, although any number of openings may be used (e.g., two, three, four, five, six, etc.).

The sealing aperture comprises a variable orifice for sealing around a wide range of medical instrument diameters. The variable orifice typically has a nominal diameter (e.g., diameter without any instrument passing therethrough) in a range from about 0.015 inch or less to about 0.220 inch or greater. Other useful ranges for the orifice nominal diameter include from about 0.020 inch to about 0.220 inch, from about 0.015 inch to about 0.050 inch, and from about 0.025 inch to about 0.035 inch. The sealing aperture provides an expansion coefficient in a range from about 500% to about 1200% or higher of the nominal diameter; more particularly from about 500% to about 700% of the nominal diameter. The variable orifice may be expansible from a first reduced diameter when no medical instrument traverses the sealing aperture (e.g., before or after instrument insertion) to a second enlarged diameter when the medical instrument traverses the sealing aperture (e.g., during instrument insertion, placement or withdrawal). The variable orifice may be capable of sealingly receiving therethrough one or more instruments having a diameter ranging from about the same or slightly larger diameter as the nominal diameter of the aperture to about twelve or more times the nominal diameter of the aperture.

In one embodiment of the present invention, the lumen may comprise an hourglass configuration having a funnel-shaped upstream lumen that converges inwardly and a funnel-shaped downstream lumen that diverges outwardly. The upstream and downstream lumens intersect at the sealing aperture. This hourglass configuration has many advantages. For example, when a medical instrument is being withdrawn through the aperture, the funnel shape of the upstream lumen reduces the possibility that any sharp edges present on the instrument will damage the valve body, thus improving the likelihood that the sealing aperture will provide a desirable fluid-tight seal around the instrument. Further, this hour glass shape has been found to help maintain the shape of the passive valve, particularly at the sealing aperture. Still further, this symmetric configuration promotes pressure normalization on either ends of the valve so as to minimize wear, tear, or further damage of the valve. In another embodiment of the present invention, the lumen comprises a conical configuration having a funnel-shaped downstream lumen, wherein the sealing aperture is positioned adjacent the upstream annulus region.

The valve embodiments of the present invention may generally be formed from silicone, rubber, a combination thereof, or like medical device grade materials that can accommodate a variety of medical instrument diameters without plastic deformation or tearing. A useful material for the valve body of the present invention comprises 40 or 50 durometer silicone rubber. The medical instrument may comprise a guidewire, catheter, or like device.

The present invention may further comprise at least one reinforcing rib extending, for example, from the valve upstream annulus region to the valve downstream annulus region. Such reinforcing ribs or like reinforcements help to maintain the axial integrity of the variable orifice. In some embodiments, a valve cartridge may further be disposed between the valve upstream annulus region and the valve downstream annulus region. The valve cartridge further inhibits leakage of fluid from or into the introducer sheath by forming an additional seal between the annulus regions. The valve cartridge may comprise any biocompatible polymer (such as polycarbonate or nylon) or like materials and may be mechanically fastened, welded, or otherwise affixed into place.

In another aspect of the present invention, a passive valve for creating a hemostatic seal around a medical instrument is provided. The valve is configured to be removably housed within an introducer sheath. The valve comprises a valve body having an upstream end and a downstream end. The valve body defines a lumen having inner and outer surfaces therethrough. The lumen may comprise an hourglass configuration having a funnel-shaped upstream lumen that converges inwardly and a funnel-shaped downstream lumen that diverges outwardly. The upstream and downstream lumens intersect at a sealing aperture configured nominally to remain open, even when no instrument traverses the valve aperture. The upstream end includes an upstream annulus region defining at least one opening and the downstream end includes a downstream annulus region. Each annulus region and lumen outer surface defines at least one chamber. The at least one opening transmits pressure from the upstream end through the upstream annulus region.

In a further aspect of the present invention, yet another passive valve for creating a hemostatic seal around a medical instrument is provided. The valve is removably housed within an introducer sheath. The valve comprises a valve body having an upstream end and a downstream end. The valve body defines a lumen having an inner and outer surface therethrough. The lumen comprises a conical configuration having a funnel-shaped downstream lumen. The upstream end includes an upstream annulus region defining at least one opening, wherein a sealing aperture is positioned between the upstream annulus region and the downstream lumen. The downstream end includes a downstream annulus region. Each annulus region and lumen outer surface defines at least one chamber. The at least one opening transmits pressure from the upstream end through the upstream annulus region.

In yet another aspect of the present invention, a medical introducer sheath is provided comprising a tubular shaft having a proximal end and a distal end. A passive hemostatic valve is removably positioned within the proximal end of the tubular shaft. The valve includes a valve body having an upstream end and a downstream end. The valve body defines a lumen having an inner and outer surface therethrough and a sealing aperture configured nominally to remain open. The upstream end includes an upstream annulus region defining at least one opening and the downstream end includes a downstream annulus region. Each annulus region and lumen outer surface defines at least one chamber. The at least one opening transmits pressure from the upstream end through the upstream annulus region so as to allow a fluid to enter the at least one chamber to equalize pressure on the upstream and downstream ends of the valve body and to enhance a hemostatic seal around an instrument. A valve cartridge is disposed between the upstream annulus region and the downstream annulus region and is removably positioned within the proximal end of the tubular shaft.

In some embodiments, the tubular shaft may be bifurcated, comprising two proximal ends. In such a case, a second passive hemostatic valve as described above may be incorporated into the bifurcated tubular shaft so that each proximal end of the tubular shaft removably receives one valve. Typically, each annulus region of the valve engages an inner lumen of the tubular body. The sealing aperture of the valve comprises a variable orifice which is expansible from a first reduced diameter to a second enlarged diameter and which has a nominal diameter range from about 0.020 inch to about 0.220 inch.

In a further aspect of the present invention, methods for creating a hemostatic seal around a medical instrument are provided. One method comprises providing a passive valve removably housed within an introducer sheath. The valve includes a valve body having an upstream end and a downstream end. The valve body defines a lumen having an inner and outer surface therethrough. The lumen comprises an hourglass configuration having a funnel-shaped upstream lumen that converges inwardly and a funnel-shaped downstream lumen that diverges outwardly. The upstream and downstream lumens intersect at a sealing aperture configured nominally to remain open. The upstream end includes an upstream annulus region having at least one opening and the downstream end includes a downstream annulus region. Each annulus region and lumen outer surface define at least one chamber. As the instrument traverses the valve, the at least one opening transmits pressure from the upstream end through the upstream annulus region so as to allow a fluid to enter the at least one chamber to equalize pressure on the upstream and downstream ends of the valve body and to enhance the hemostatic seal around the instrument.

In still a further aspect of the present invention, a method for assembling a medical device is provided. An introducer sheath is provided within which a passive valve is housed. The valve includes a valve body having an upstream end and a downstream end. The valve body defines a lumen having an inner and outer surface therethrough. The lumen comprises an hourglass configuration having a funnel-shaped upstream lumen that converges inwardly and a funnel-shaped downstream lumen that diverges outwardly. The upstream and downstream lumens intersect at a sealing aperture configured nominally to remain open. The upstream end includes an upstream annulus region having at least one opening and the downstream end includes a downstream annulus region. Each annulus region and lumen outer surface defines at least one chamber. A medical instrument is further provided for positioning through the valve. The at least one opening transmits pressure from the upstream end through the upstream annulus region so as to allow a fluid to enter the at least one chamber to equalize pressure on the upstream and downstream ends of the valve body and to enhance the hemostatic seal around the instrument.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

The present invention provides vascular introducer sheaths incorporating improved hemostatic passive valves for use in endovascular, laparoscopic, and other medical procedures. Vascular sheaths generally provide access to a body lumen (e.g., a blood vessel), cavity, or organ for the delivery of medical instruments, such as guidewires, catheters, etc. that may further contain devices such as stents, stent-grafts, balloons, etc. The hemostatic valve may be releasable from the introducer sheath or be an integral part of the introducer sheath. The hemostatic valves may further be incorporated into any portion of the sheath (e.g., hub or shaft), at a common position or at a different position. The hemostatic valves of the present invention provide secure and reliable sealing so as to minimize leakage of fluid from (e.g., back bleeding) or into the introducer sheath when medical instruments or tools are inserted into or withdrawn from the sealing valve. Further, the valves of the present invention are adapted to seal about a wide variety of medical instruments having a wide range of instrument diameters. It will be appreciated that the hemostatic valves of the present invention may also be incorporated into a number of different of medical devices, such as bifurcated sheaths, catheters, cannulas, trocar assemblies, and other tubular medical devices, and are not limited to incorporation with an introducer sheath.

Figure 1A:
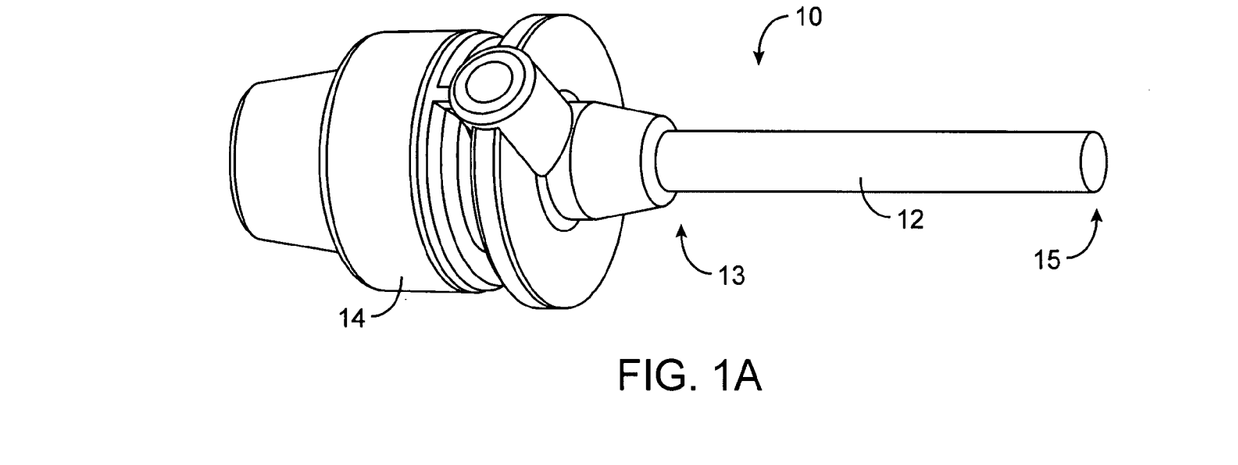
FIGS. 1A and 1B are perspective illustrations of an introducer sheath with which various embodiments of the present invention may be used.
Figure 1B:
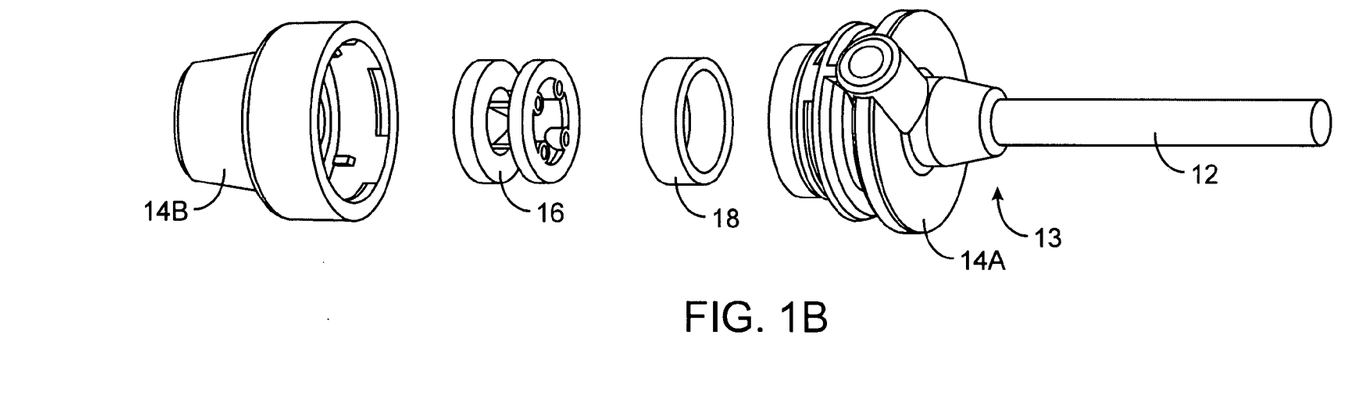

Referring now to FIGS. 1A and 1B, an exemplary introducer sheath 10 with which various embodiments of the present invention may be used is illustrated. The introducer sheath 10 generally comprises a tubular shaft 12 having a proximal end 13 and a distal end 15 and a two-piece hub 14 that is adapted for coupling to the proximal end 13 of shaft 12. Hub 14 comprises hub main body 14A and cap 14B which may be coupled to one another by any appropriate means, such as by threading or, as shown in FIGS. 1A and 1B, by being press fit or mechanically snapped into place. The sheath 10 may be formed from a variety of medical grade materials. Particularly useful for the present invention is a composite sheath comprising an inner liner, a braid, and an outer layer. The inner liner is made of biocompatible lubricious polymers such as fluoropolymers (e.g., polytetrafluoroethylene or PTFE), fluorinated ethylene propylene (FEP), or high density polyethylene. The liner may also be filled with a radiopaque material such as barium sulfate or the like. The braid may be any number of materials such as stainless steel, etc. and may be in a ribbon form. The outer layer is made of a bondable polymer such as nylon or fluoropolymers such as PEBAX®. Other sheath materials and configurations may be used.

Figures 4A, 4B, 4C:
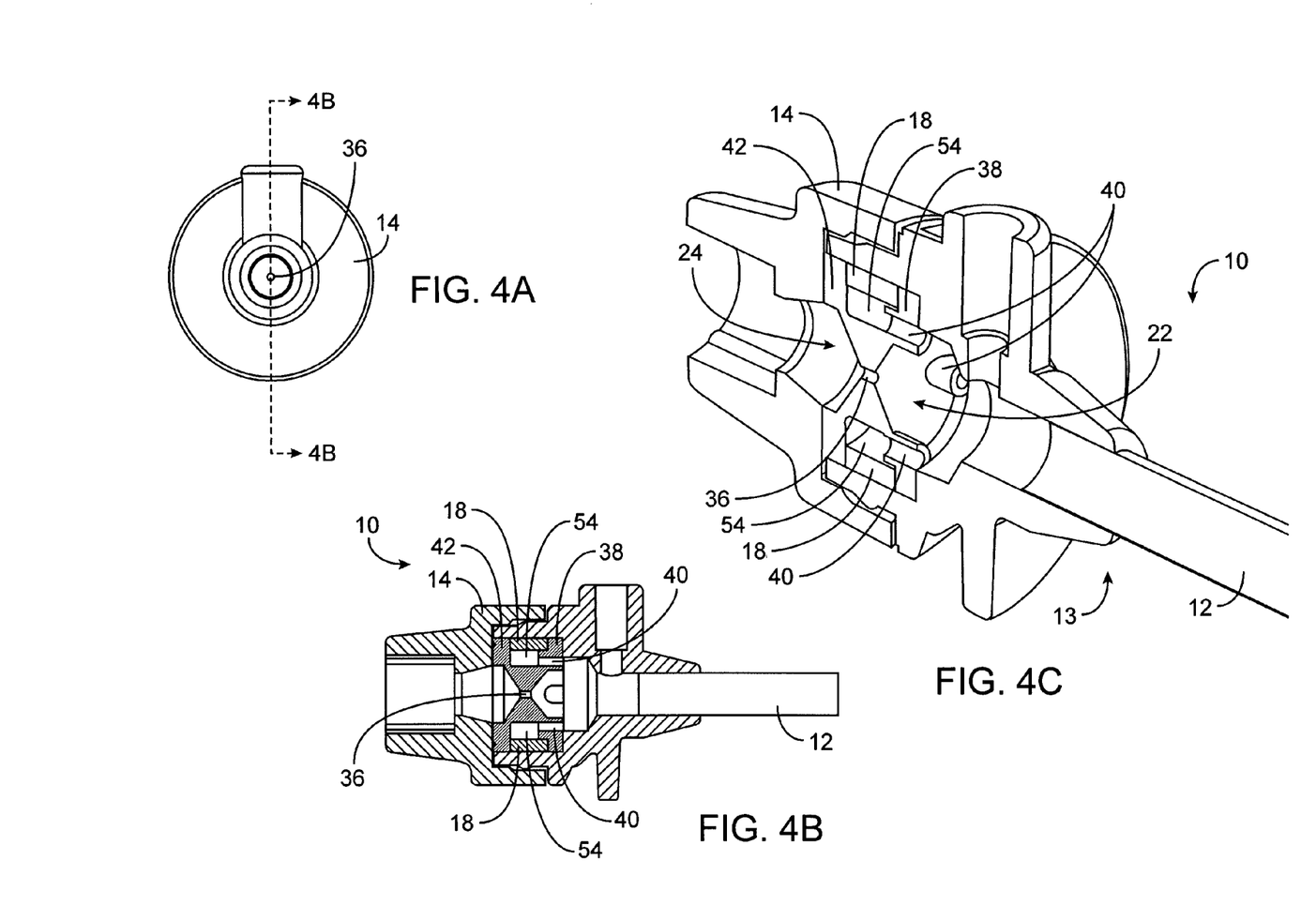
FIGS. 4A–4C are cross-sectional views of an introducer sheath housing the passive hemostatic sheath valve of FIGS. 2A–2F.

As shown in FIG. 1B, a passive hemostatic valve 16 as described in more detail below may removably be positioned at a proximal portion 13 of the introducer sheath 10 within the hub 14. As noted above, the valve 16 may alternatively be integrally formed within the sheath 10 and positioned at any desired portion of the sheath 10. As shown in FIGS. 1B, 4B and 4C, a valve cartridge 18 may also be removably positioned integral with valve 16 as will be described in more detail below. The valve cartridge 18 may be formed from a variety of biocompatible materials including polymers (such as polycarbonate or nylon) and is removably positioned into place. It will be appreciated that the above depictions are for illustrative purposes only and do not necessarily reflect the actual shape, size, or dimensions of the sheath 10, valve 16, or cartridge 18. For example, the shaft 12 has a greater length than illustrated in FIGS. 1A and 1B. This applies to all depictions herein.

Referring now to FIGS. 2A through 2F, a passive hemostatic sheath valve 16 in accordance with one embodiment of the present invention is illustrated. The valve 16 for creating a hemostatic seal around a medical instrument comprises a valve body 20 having an upstream end 22 and a downstream end 24. The valve body 20 defines a lumen 26 having an inner surface 28 and an outer surface 30 therethrough. The lumen 26 comprises an hourglass configuration having a funnel- or conical-shaped upstream lumen 32 that converges inwardly and a funnel-shaped downstream lumen 34 that diverges outwardly. The upstream and downstream lumens 32, 34 intersect at a sealing aperture or hole 36 configured nominally to remain open (i.e., prior to, during, and subsequent to device insertion). The upstream end 22 includes an upstream annulus region 38 defining at least one opening 40 and the downstream end 24 includes a downstream annulus region 42.

Figure 2A:
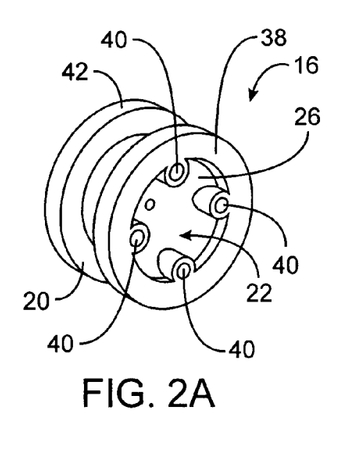
FIGS. 2A–2F are perspective, plan, and cross-sectional illustrations of a passive hemostatic sheath valve in accordance with one embodiment of the present invention.
Figure 2B:
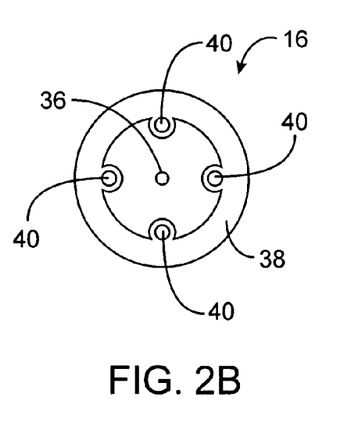
Figure 2C:
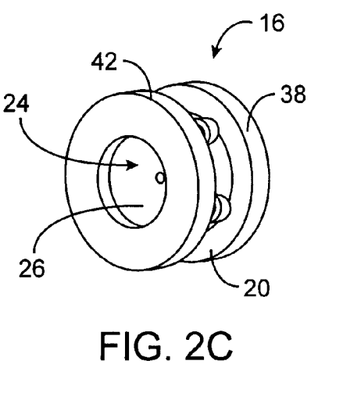

As shown in FIG. 2B, the valve 16 of this embodiment includes four openings 40 within the upstream end 22 that are symmetrically-spaced so as to promote equal stress distribution within the valve body. However, it will be appreciated that any number of openings 40 may be utilized (e.g., from two to six or more) on either end 22, 24 of the valve body 20 to achieve the desired pressure equalization, in any configuration, as discussed in more detail below. The openings 40 typically will have a diameter in a range from about 0.005 inch to about 0.080 inch; more particularly from about 0.030 inch to about 0.055 inch.

Figure 2D:
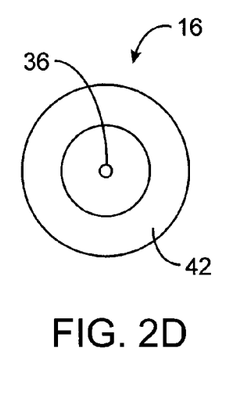
Figure 2E:
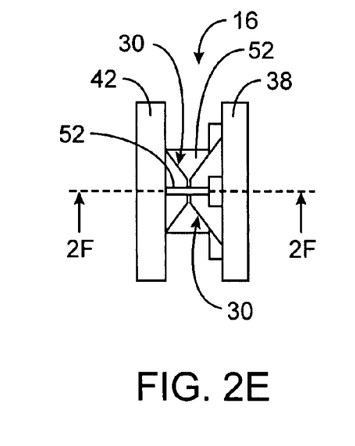
Figure 2F:
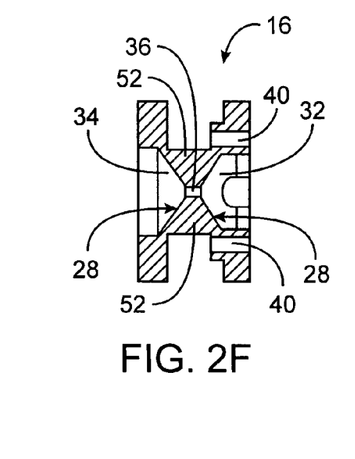
Figure 3A:
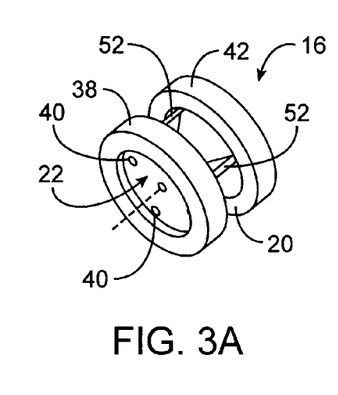
FIGS. 3A–3F are perspective, plan, and cross-sectional illustrations of a passive hemostatic sheath valve in accordance with another embodiment of the present invention.
Figure 3B:
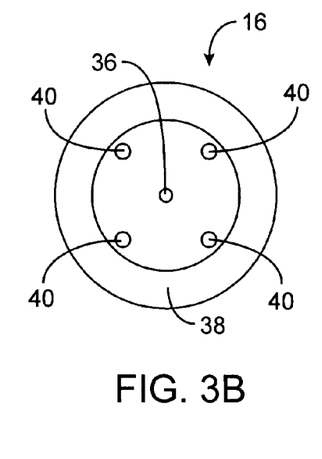
Figure 3C:
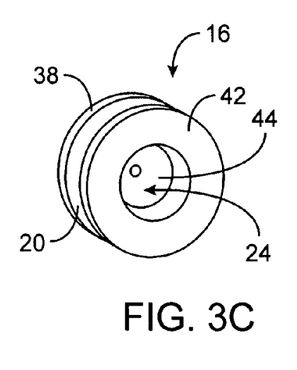
Figure 3D:
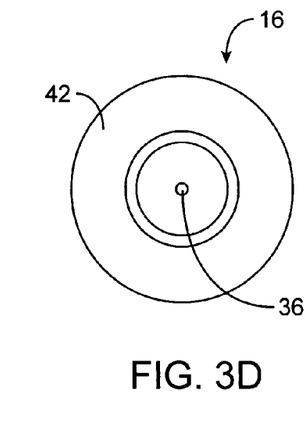
Figure 3E:
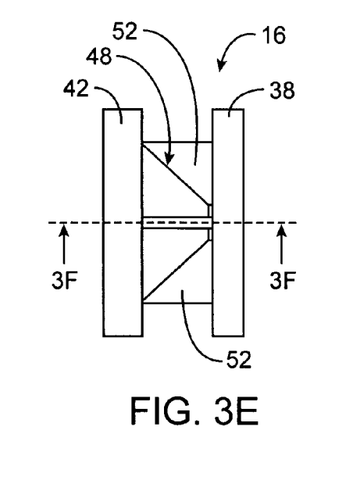
Figure 3F:
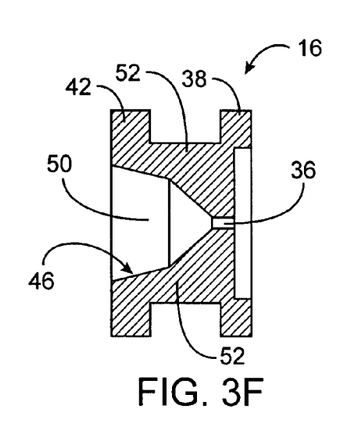

As shown in the view of FIG. 2D, the sealing aperture 36 comprises an orifice capable of accommodating and providing a fluid-tight seal around a wide range of medical instrument diameters. The variable orifice typically has a nominal diameter (e.g., diameter without any instrument passing therethrough) in a range from about 0.015 inch to about 0.220 inch. Other useful ranges for the orifice nominal diameter include from about 0.020 inch to about 0.220 inch, from about 0.015 inch to about 0.050 inch, and from about 0.025 inch to about 0.035 inch. The sealing aperture provides an expansion coefficient in a range from about 500% to about 1200% or higher of the nominal diameter; more particularly from about 500% to about 700% of the nominal diameter. The variable orifice may be expansible from a first reduced diameter when no medical instrument traverses the sealing aperture (e.g., before or after instrument insertion) to a second enlarged diameter when the medical instrument traverses the sealing aperture (e.g., during instrument insertion, placement or withdrawal).

Referring now to FIGS. 3A through 3F, a passive hemostatic sheath valve 16 in accordance with another embodiment of the present invention is illustrated. The passive valve 16 for creating a hemostatic seal around a medical instrument comprises a valve body 20 having an upstream end 22 and a downstream end 24. The valve body 20 defines a lumen 44 having an inner surface 46 and an outer surface 48 therethrough. The lumen 44 comprises a conical or funnel configuration having a funnel-shaped downstream lumen 50. The upstream end 22 includes an upstream annulus region 38 defining at least one opening 40, wherein a sealing aperture 36 is positioned between the upstream annulus region 38 and the downstream lumen 50. The downstream end 24 includes a downstream annulus region 42.

As shown in FIGS. 3E, 3F, 2E, and 2F, the valves 16 of the present invention may further comprise at least one reinforcing rib 52 extending from the upstream annulus region 38 to the downstream annulus region 42. The valve 16 comprises four reinforcing ribs 52, however, it will be appreciated that any desired number of reinforcing ribs 52 may be utilized (e.g., two to six or more). Such reinforcing ribs 52 or the like help maintain the axial integrity of orifice 36. The valve embodiments 16 of the present invention are generally formed from silicone, rubber, a combination thereof, or like medical device grade materials that can accommodate a variety of medical instrument diameters without plastic deformation or tearing. A useful material of the valve body 20 comprises 40 or 50 durometer silicone rubber.

Referring now to FIGS. 4A through 4C, views of an introducer sheath 10 housing the passive hemostatic sheath valve 16 of FIGS. 2A–2F are illustrated. As can be seen in the cross sectional views of FIGS. 4B and 4C, each annulus region 38, 42 and lumen outer surface 30 define a chamber 54. The openings 40 transmit pressure from the upstream end 22 via the upstream annulus region 38 so as to allow a fluid (e.g., blood or air) to enter the chamber 54 as a greater pressure is generally on the upstream side 22. Pressure from the fluid entering the chamber 54 symmetrically seals the walls of aperture 36 around the instrument. Hence, the opening 40 advantageously allows for pressure equalization on the upstream 22 and downstream 24 ends of the valve body 20 so that the valve body is less likely to inflate and leak fluids from or into the introducer sheath 10 when medical tools are inserted into or withdrawn from the sealing aperture 36. In this illustration, the valve cartridge 18 is disposed between the upstream annulus region 38 and the downstream annulus region 42 and within the hub 14 so as to form a boundary of the chamber 54. As such, the cartridge 18 further helps create a seal around the aperture 36 that inhibits leakage of fluid from or into the introducer sheath 10, particularly in the case of instruments having a diameter which is the same or nearly the same as the orifice nominal diameter. In particular, the valve cartridge 18 helps maintain the integrity of orifice 36 by redistributing forces away from the aperture so that it remains intact. It will be appreciated that the hub 14 may also form a boundary of the chamber 54 in the absence of a valve cartridge 18.

Figure 5A:
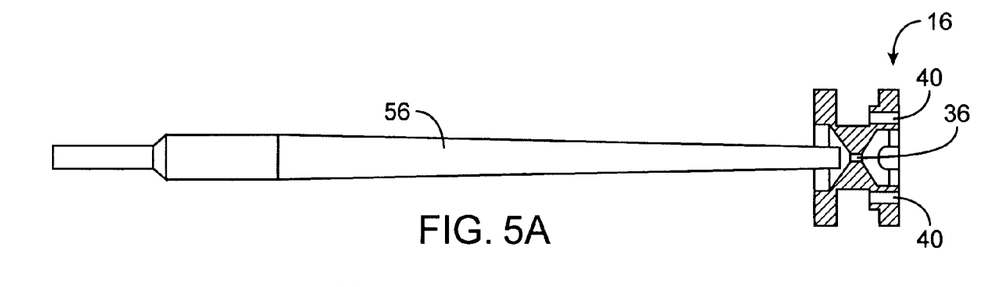
FIGS. 5A–5C are cross-sectional views illustrating a method for creating a hemostatic seal around a medical instrument in accordance with methods of the present invention.
Figure 5B:
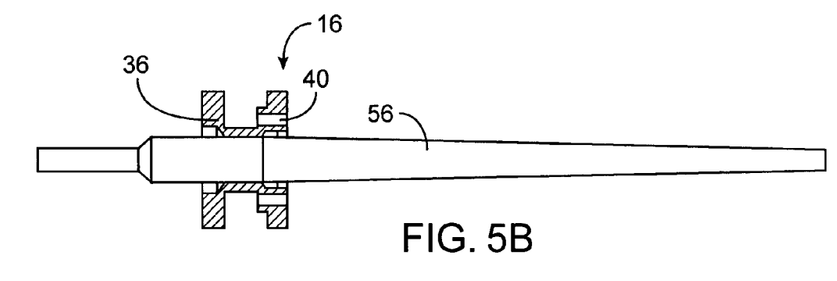
Figure 5C:
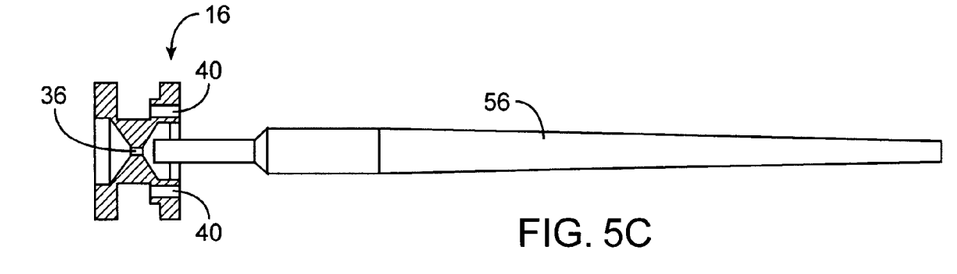

Referring now to FIGS. 5A through 5C, cross-sectional views of an exemplary method for creating a hemostatic seal around a medical instrument 56 are illustrated. This method comprises providing a passive valve 16 as previously described above in detail. For purposes of illustration only, the valve embodiment of FIGS. 2A through 2F are shown, although the valve embodiment of FIGS. 3A through 3F may be used as well. As the instrument 56 traverses the valve 16, as seen in FIG. 5B, the at least one opening 40 transmits pressure from the upstream end 22 through the upstream annulus region 38 so as to allow a fluid to enter the chamber 54 (FIGS. 4B and 4C) to equalize pressure on the upstream 22 and downstream 24 ends of the valve body 20 and to enhance the hemostatic seal around the instrument 56. The variable orifice 36 may be capable of sealingly receiving therethrough one or more instruments 56 having a diameter ranging from about 0.005 inch greater than the nominal diameter of orifice 36 (FIGS. 5A and 5C) to about eight or more times the nominal diameter of the orifice (FIG. 5B). A hemostatic seal may be achieved even when instrument 56 diameter is the same or nearly the same as the nominal diameter of orifice 36. It is believed that the design features of the present invention, including the fluid pressurization of chamber 54 via opening or openings 40 during use allows aperture 36 to retain its axial integrity and seal around the instrument 56. The instrument 56 may comprise a variety of tools as small as a guidewire and up to large delivery catheters. Typically, during a medical procedure, the guidewire remains traversed through the aperture 36.

Figure 6A:
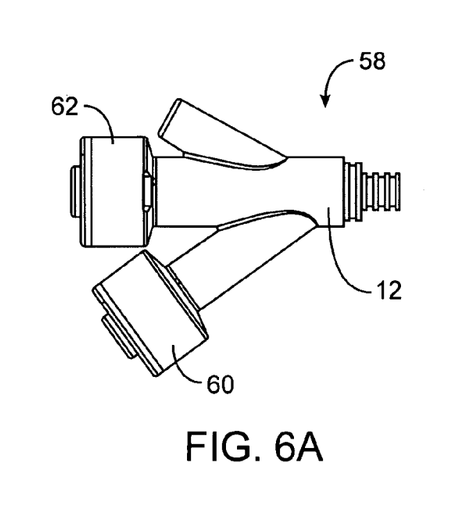
FIGS. 6A–6D are plan, side, and cross-sectional illustrations of a bifurcated introducer sheath with which various embodiments of the present invention may be used.
Figure 6B:
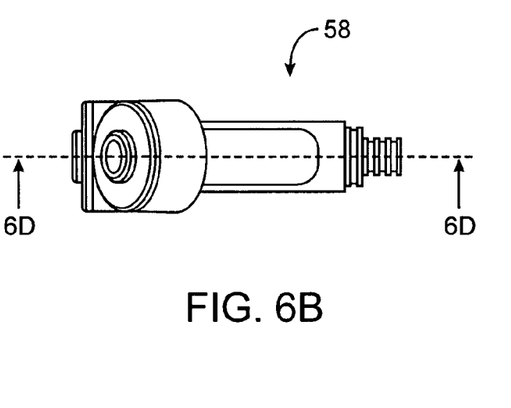
Figure 6C:
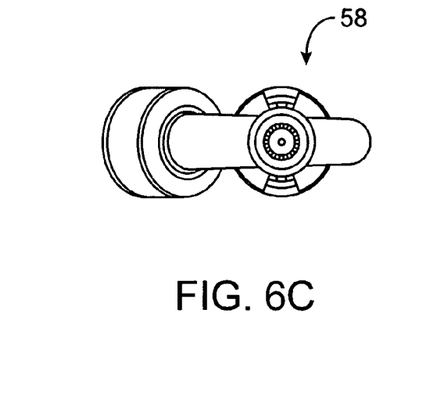
Figure 6D:
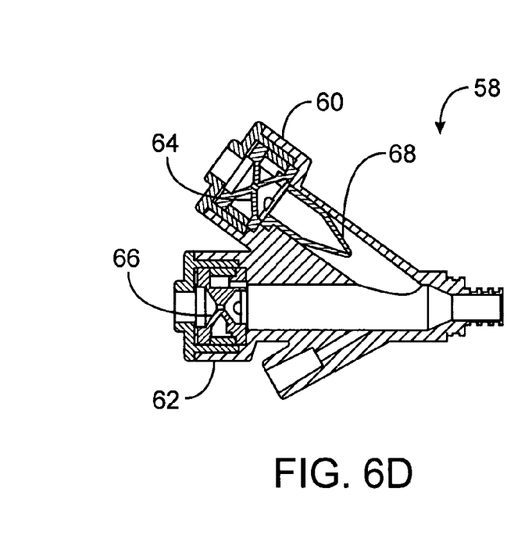

FIGS. 6A–6D are plan, side, and cross-sectional illustrations of a bifurcated introducer sheath 58 with which various embodiments of the present invention may be used. In this embodiment, the sheath 58 may be bifurcated comprising at least two hubs 60, 62 coupleable to a proximal end of the shaft 12. As shown in FIG. 6D, a first passive hemostatic valve 64 is incorporated into to the first hub 60 and a second passive hemostatic valve 66 is incorporated into to the second hub 62. Each annulus region of the valves 64, 66 is removably received within an inner lumen of the respective hubs 60, 62. The valves 64, 66 may comprise any of embodiments described herein. Additionally, a conventional duct bill valve 68 may be removably received within one end (or both ends) of the bifurcated sheath 58 to prevent any fluid leakage from or into the shaft 12 when no instrument is traversing the valve 64.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A passive valve for creating a hemostatic seal around a medical instrument, the valve configured to be housed within an introducer sheath, the valve comprising:
    a valve body having an upstream end, a downstream end, and a lumen having an inner and outer surface therethrough, the valve body defining a sealing aperture configured nominally to remain open;
    wherein the upstream end includes an upstream annulus region defining at least one opening;
    wherein the downstream end includes a downstream annulus region;
    wherein each annulus region and lumen outer surface define at least one chamber, the at least one opening transmitting pressure from the upstream end through the upstream annulus region so as to allow a fluid to enter the at least one chamber; and
    a valve cartridge disposed between the upstream annulus region and the downstream annulus region.

2. A valve as in claim 1 wherein the sealing aperture comprises a variable orifice which is expansible from a first reduced diameter to a second enlarged diameter.

3. A valve as in claim 1 wherein the sealing aperture comprises a variable orifice having a nominal diameter in a range from about 0.020 inch to about 0.220 inch.

4. A valve as in claim 3 wherein the sealing aperture has an expansion coefficient in a range from about 500% to about 700% of the nominal diameter.

5. A valve as in claim 3 wherein the sealing aperture further comprises a variable orifice capable of sealingly receiving therethrough one or more instruments having a diameter ranging from about the same diameter as the nominal diameter of the aperture to about eight times the nominal diameter of the aperture.

6. A valve as in claim 1 wherein the lumen comprises an hourglass configuration having a funnel-shaped upstream lumen that converges inwardly and a funnel-shaped downstream lumen that diverges outwardly, the upstream and downstream lumens intersecting at the sealing aperture.

7. A valve as in claim 1 wherein the lumen comprises a conical configuration having a funnel-shaped downstream lumen, wherein the sealing aperture is positioned adjacent the upstream annulus region.

8. A valve as in claim 1 wherein the valve body comprises silicone, rubber, or a combination thereof.

9. A valve as in claim 1 wherein the instrument comprises a guidewire or a catheter.

10. A valve as in claim 1 further comprising at least one reinforcing rib extending from the upstream annulus region to the downstream annulus region.

11. A valve as in claim 1 wherein the valve cartridge comprises biocompatible polymer.

12. A medical introducer sheath comprising:
    a tubular shaft having a proximal end and a distal end;
    a passive hemostatic valve positioned within the proximal end of the tubular shaft, the valve including:
    a valve body having an upstream end and a downstream end, the valve body defining a lumen having an inner and outer surface therethrough and a sealing aperture configured nominally to remain open;
    wherein the upstream end includes an upstream annulus region defining at least one opening;
    wherein the downstream end includes a downstream annulus region; and wherein each annulus region and lumen outer surface define at least one chamber, the at least one opening transmitting pressure from the upstream end through the upstream annulus region so as to allow a fluid to enter the at least one chamber to equalize pressure on the upstream and downstream ends of the valve body and to enhance a hemostatic seal around an instrument; and
    a valve cartridge disposed between the upstream annulus region and the downstream annulus region and positioned within the proximal end of the tubular shaft.

13. An introducer sheath as in claim 12 wherein the tubular shaft is bifurcated comprising two proximal ends.

14. An introducer sheath as in claim 13 further comprising a second passive hemostatic valve, wherein each proximal end of the tubular shaft receives one valve.

15. An introducer sheath as in claim 12 wherein each annulus region of the valve engages an inner lumen of the tubular body.

16. An introducer sheath as in claim 12 wherein the sealing aperture of the valve comprises a variable orifice which is expansible from a first reduced diameter to a second enlarged diameter.

17. An introducer sheath as in claim 16 wherein the variable orifice has a nominal diameter in a range from about 0.020 inch to about 0.220 inch.

18. A passive valve for creating a hemostatic seal around a medical instrument, the valve configured to be removably housed within an introducer sheath, the valve comprising:
    a valve body having an upstream end, a downstream end, and a lumen having an inner and outer surface therethrough, the valve body defining a sealing aperture configured nominally to remain open;
    wherein the upstream end includes an upstream annulus region defining at least four openings;
    wherein the downstream end includes a downstream annulus region; and
    wherein each annulus region and lumen outer surface define at least one chamber, wherein at least one opening transmits pressure from the upstream end through the upstream annulus region so as to allow a fluid to enter the at least one chamber.

* * * * *